US009029345B2

(12) United States Patent
Berdis et al.

(10) Patent No.: US 9,029,345 B2
(45) Date of Patent: May 12, 2015

(54) SELECTIVE INHIBITORS OF TRANSLESION DNA REPLICATION

(75) Inventors: Anthony J. Berdis, Cleveland Heights, OH (US); Irene Lee, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 1760 days.

(21) Appl. No.: 12/515,382

(22) PCT Filed: Nov. 16, 2007

(86) PCT No.: PCT/US2007/084952
§ 371 (c)(1),
(2), (4) Date: Mar. 2, 2012

(87) PCT Pub. No.: WO2008/147454
PCT Pub. Date: Dec. 4, 2008

(65) Prior Publication Data
US 2010/0111839 A1 May 6, 2010

Related U.S. Application Data

(63) Continuation-in-part of application No. PCT/US2006/009364, filed on Mar. 15, 2006.

(60) Provisional application No. 60/859,411, filed on Nov. 16, 2006, provisional application No. 60/662,311, filed on Mar. 16, 2005.

(51) Int. Cl.
| | |
|---|---|
| *A01N 43/04* | (2006.01) |
| *A61K 31/70* | (2006.01) |
| *A61K 31/7052* | (2006.01) |
| *C07H 19/16* | (2006.01) |
| *C07H 19/173* | (2006.01) |
| *C07H 19/20* | (2006.01) |
| *A61K 31/7056* | (2006.01) |

(52) U.S. Cl.
CPC ............... *A61K 31/70* (2013.01); *C07H 19/16* (2013.01); *A61K 31/7052* (2013.01); *C07H 19/173* (2013.01); *C07H 19/20* (2013.01); *A61K 31/7056* (2013.01)

(58) Field of Classification Search
None
See application file for complete search history.

(56) References Cited

U.S. PATENT DOCUMENTS

| | | | |
|---|---|---|---|
| 5,401,724 | A | 3/1995 | Beutler |
| 5,446,139 | A | 8/1995 | Seela et al. |
| 5,478,852 | A | 12/1995 | Olefsky et al. |
| 5,705,490 | A | 1/1998 | Townsend et al. |
| 6,153,594 | A | 11/2000 | Hydro |
| 5,478,852 | C1 | 3/2001 | Olefsky et al. |
| 6,548,486 | B1 | 4/2003 | Dalen |
| 2005/0272676 | A1 | 12/2005 | Bhat et al. |
| 2006/0025375 | A1 | 2/2006 | Gosselin et al. |
| 2007/0259832 | A1 | 11/2007 | Cook et al. |
| 2009/0048202 | A1 | 2/2009 | Berdis et al. |

FOREIGN PATENT DOCUMENTS

WO  WO 98/39967  9/1998

OTHER PUBLICATIONS

Costigan, Christine, et al., "*A Synthetic Lethal Screen Identifies SLK1, a Novel Protein Kinase Homolog Implicated in Yeast Cell Morphogenesis and Cell Growth*", Molecular and Cellular Biology, Mar. 1992, p. 1162-1178.
Cottam, Howard B., et al., "*Synthesis of 2'-Deoxyribofuranosyl Indole nucleotides Related to the Antibiotics SF-2140 and Neosidomycin*", Journal of Heterocyclic Chemistry, vol. 25, pp. 361-366, 1998.
Devadoss, Babho, et al., "*Is a Thymine Dimer Replicated via a Transient Abasic Site Intermediate? A Comparitivs Study Using Non-Natural Nucloetides*", Biochemistry 2007, 46, 4486-4498.
Grieb, Pawel, et al., "*5'Esters of 2'deoxyadenosine and 2-chloro-2'-deoxyadenosine with cell differentiation-provoking agents*", Acta Biochimica Polonica, vol. 49, No. Jan. 2002, p. 129-137.
Reineks et al., "*Evaluating the Contribution of Base Stacking during Translesion DNA Replication*", Biochemistry, vol. 43 pp. 393-404, 2004.
Zhang Xuemei, et al., "*Rational Attempts to Optimize Non-Natural Nucleotides for Selective Incorporation Opposite an Abasic Site*", Biochemistry 2006, 45, 13293-13303.
Zhang Xuemei, et al., "*Hydrophobocity, Shape, and Π-Electron Contributions during Translesion DNA Synthesis*", J. Am. Chem. Soc. 2006. 128, 143-149.
Zhang, Xuemei, et al., "*A Potential Chemotherapeutic Strategy for the Selective Inhibition of Promutagenic DNA Synthesis by Non-natural Nucleotides*", Biochemistry 2005, 44, 13111-13121.
Girgis, N.S., et al., "Synthesis of 2'deoxyribofuranosyl indole nucleosides related to the antibiotics SF-2140 and neosidomycin", Journal of Heterocyclic Chemistry, 2009, vol. 25, No. 2, pp. 361-366.
Motea, E.A., et al., "A non-natural nucleoside with combined therapeutic and diagnostic activities against leukemia", ACS Chemical Biology, Mar. 5, 2012, vol. 7, No. 6, pp. 988-998.

*Primary Examiner* — Patrick Lewis
(74) *Attorney, Agent, or Firm* — Tarolll, Sundheim, Covell & Tummino LLP

(57) ABSTRACT

An agent for inhibiting P-glycoproteins comprises a non-natural adenine ribose analog.

22 Claims, 7 Drawing Sheets

15 min post-treatment

A. CEM7
B. CEM/VBL
C. CEM/VBL + 50 μg/ml 5-CHInd

SELECTIVE INHIBITORS OF TRANSLESION DNA REPLICATION

RELATED APPLICATIONS

This application claims priority from U.S. Provisional Application No. 60/859,411, filed Nov. 16, 2006, and is a continuation in part of PCT International Application PCT/US2006/009364 filed Mar. 15, 2006, and U.S. Provisional Patent Application Ser. No. 60/662,311, filed Mar. 16, 2005, all of which are herein incorporated by reference in their entirety.

This invention was made with government support under Grant No. RO1 CA118408 awarded by the National Institutes of Health. The United States government has certain rights in the invention.

FIELD OF THE INVENTION

The present invention relates to selective inhibitors of P-glycoprotein and to methods of using such inhibitors for therapeutic applications.

BACKGROUND

Cancer is a disease of heterogeneous genetic origin involving the transformation of one's own cells into a malignant entity. A nearly universal feature of cancer involves the deregulation of various growth and proliferation pathways. This commonality has led to the implementation of two general chemotherapeutic strategies to treat cancer. The first approach inhibits the process of cell division by using agents, such as microtubule inhibitors, DNA alkylating agents, and ionizing radiation that target all rapidly dividing cells. Although these agents are generally efficacious over a broad range of malignancies, the lack of selectivity can unfortunately cause severe dose-limiting side effects, such as alopecia, anemia, and GI discomfort. An alternative strategy is to directly target a specific gene product that is deregulated in a specific type of cancer. An example of this strategy is imatinib (GLEEVAC). By selectively inhibiting the BCR-ABL fusion protein, imatinib is highly specific for chronic myelogenous leukemia (CML) cells with minimal side-effects compared to standard chemotherapy regiment. Unfortunately, imatinib cannot be widely used to treat other types of leukemia. The deficiencies associated with either therapeutic strategy emphasize the need to develop new chemotherapeutic agents that are broad-spectrum and possess a low potential for side-effects.

Although side effects are an obvious complication with chemotherapy, the most serious complication is the development of drug resistance. This type of resistance confers a broad spectrum of cross-resistance to many classes of drugs as they are actively exporting from the cell. This type of resistance, referred to as multi-drug resistance (MDR) phenotype, is exceptionally dangerous since the cancer can become resistant to numerous chemotherapeutic agents.

SUMMARY OF THE INVENTION

The present invention relates to a method of inhibiting P-glycoprotein activity in a cell expressing P-glycoprotein. The method includes administering to the cell a pharmaceutical composition comprising a nucleoside analog having the formula (I):

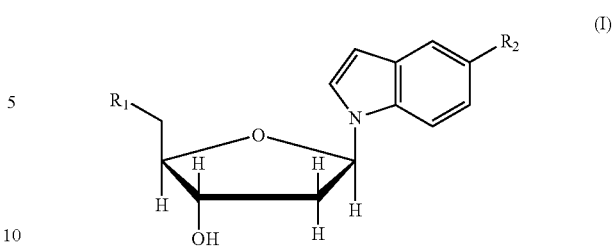

where $R_1$ is OH, monophosphate ($H_2O_3PO-$ or ($O_3PO-$)$^{2-}$), diphosphate ($H_3(O_3PO)_2-$ or (($O_3PO)_2-$)$^{3-}$), triphosphate ($H_4(O_3PO)_3-$, (($O_3PO)_3-$)$^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative; and where $R_2$ is an unsubstituted or substituted cyclohexyl; a pharmaceutically acceptable salt thereof; or a prodrug thereof.

In an aspect of the invention, the cells can comprise neoplastic cells of a subject. The nucleoside analog can competitively inhibit in the cells a first chemotherapeutic target by selectively binding to an active site of the first chemotherapeutic target and competitively inhibit a second chemotherapeutic target by selectively binding to an active site of the second chemotherapeutic target. The active site of the first chemotherapeutic target and the second chemotherapeutic target can be ATP binding regions. In a further aspect, the first chemotherapeutic target can be P-glycoprotein drug transporter and the second chemotherapeutic target can be a cyclin-dependent kinase. The cyclin-dependent kinase targeted can be selected from a group consisting of CDK1, CDK4, and CDK5 or a combination thereof. The nucleoside analog can be administered to the subject at a dosage in the range of about 0.001 µg/mL/day to about 100 µg/mL/day.

In yet another aspect, the nucleoside analog can comprise:

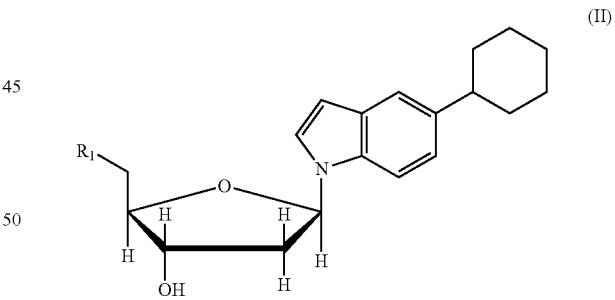

where $R_1$ is OH, monophosphate ($H_2O_3PO-$ or ($O_3PO-$)$^{2-}$), diphosphate ($H_3(O_3PO)_2-$ or (($O_3PO)_2-$)$^{3-}$), triphosphate ($H_4(O_3PO)_3-$, (($O_3PO)_3-$)$^{4-}$), or $OR_a$, where $R_a$ comprises at least one of a straight chain, branched or cylclic alkyl, CO-alkyl, CO-aryl, CO-alkoxyalkyl, arylsulfonyl, aralkylsulfonyl, amino acid residude, fatty acid residue, or a mono, di, or triphosphate derivative; a pharmaceutically acceptable salt thereof; or a prodrug thereof.

The present invention also relates to a method of treating a neoplastic disorder in a subject. The method includes administering to neoplastic cells of the subject a pharmaceutical composition comprising a nucleoside analog having the formula (I):

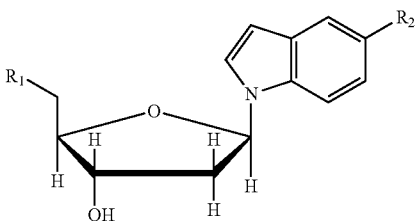

where $R_1$ is OH, monophosphate ($H_2O_3PO-$ or ($O_3PO-$)$^{2-}$), diphosphate ($H_3(O_3PO)_2-$ or (($O_3PO)_2-$)$^{3-}$), triphosphate ($H_4(O_3PO)_3-$, (($O_3PO)_3-$)$^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative; and where $R_2$ is an unsubstituted or substituted cyclohexyl; a pharmaceutically acceptable salt thereof; or a prodrug thereof.

In an aspect of the invention, the neoplastic cell can express P-glycoprotein. The nucleoside analog can competitively inhibit in the cells a first chemotherapeutic target by selectively binding to an active site of the first chemotherapeutic target and competitively inhibit a second chemotherapeutic target by selectively binding to an active site of the second chemotherapeutic target. The active site of the first chemotherapeutic target and the second chemotherapeutic target can ATP binding regions. In a further aspect, the first chemotherapeutic target can be P-glycoprotein drug transporter and the second chemotherapeutic target can be a cyclin-dependent kinase. The cyclin-dependent kinase targeted can be selected from a group consisting of CDK1, CDK4, and CDK5 or a combination thereof. The nucleoside analog can be administered to the subject at a dosage in the range of about 0.001 µg/mL/day to about 100 µg/mL/day.

In another aspect of the invention, the nucleoside analog can be administered in conjunction with another therapeutic agent. The other therapeutic agents can comprise at least one of a chemotherapeutic agent, an antimetabolite, an antitumorgenic agent, an antimitotic agent, an antiviral agent, an antineoplastic agent, an immunotherapeutic agent, and/or a radiotherapeutic agent. In one example, the other therapeutic agent can be a substrate for P-glycoprotein. In another example, the therapeutic agent can comprise at least one of vinblastine, doxorubicin, etoposide, taxol, paclitaxel, and/or combinations thereof.

The present invention further relates to a pharmaceutical composition that comprises a nucleoside analog that inhibits multiple chemotherapeutic targets having the formula (I):

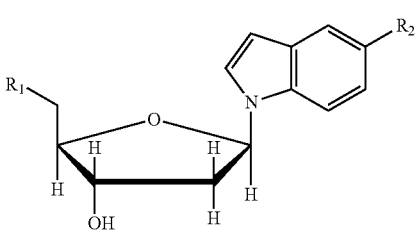

where $R_1$ is OH, monophosphate ($H_2O_3PO-$ or ($O_3PO-$)$^{2-}$), diphosphate ($H_3(O_3PO)_2-$ or (($O_3PO)_2-$)$^{3-}$), triphosphate ($H_4(O_3PO)_3-$, (($O_3PO)_3-$)$^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative; and where $R_2$ is an unsubstituted or substituted cyclohexyl; a pharmaceutically acceptable salt thereof; or a prodrug thereof.

In an aspect of the invention, the nucleoside analog can inhibit multiple ATPases when administered to a neoplastic cell. In one example, the nucleoside analog can inhibit P-glycoprotein drug transporter and a cyclin-dependent kinase.

In another aspect, the nucleoside analog can comprise:

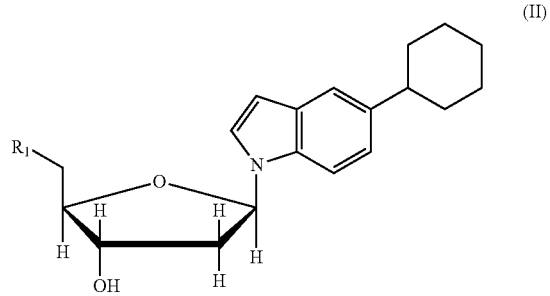

where $R_1$ is OH, monophosphate ($H_2O_3PO-$ or ($O_3PO-$)$^{2-}$), diphosphate ($H_3(O_3PO)_2-$ or (($O_3PO)_2-$)$^{3-}$), triphosphate ($H_4(O_3PO)_3-$, (($O_3PO)_3-$)$^{4-}$), or $OR_a$, where $R_a$ comprises at least one of a straight chain, branched or cylclic alkyl, CO-alkyl, CO-aryl, CO-alkoxyalkyl, arylsulfonyl, aralkylsulfonyl, amino acid residude, fatty acid residue, or a mono, di, or triphosphate derivative; a pharmaceutically acceptable salt thereof; or a prodrug thereof.

The present invention further relates to a method of potentiating the cytotoxic effect of chemotherapeutic agents on multiple drug resistant neoplastic cells. The method includes administering a nucleoside analog to the subject in conjunction with administering a chemotherapeutic agent. The nucleoside analog can have the formula (I):

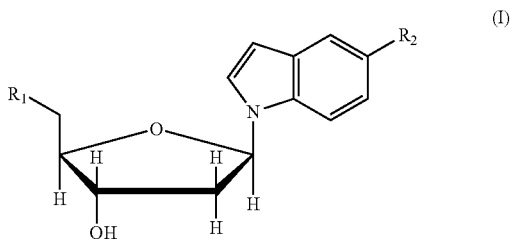

where $R_1$ is OH, monophosphate ($H_2O_3PO-$ or ($O_3PO-$)$^{2-}$), diphosphate ($H_3(O_3PO)_2-$ or (($O_3PO)_2-$)$^{3-}$), triphosphate ($H_4(O_3PO)_3-$, (($O_3PO)_3-$)$^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative; and where $R_2$ is an unsubstituted or substituted cyclohexyl; a pharmaceutically acceptable salt thereof; or a prodrug thereof.

The chemotherapeutic agent can include at least one of an antimetabolite, an antitumorgenic agent, an antimitotic agent, an antiviral agent, an antineoplastic agent, an immunotherapeutic agent, or a radiotherapeutic agent. In an aspect of the invention, the chemotherapeutic agent can be a substrate for P-glycoprotein.

DETAILED DESCRIPTION

Figure 1:
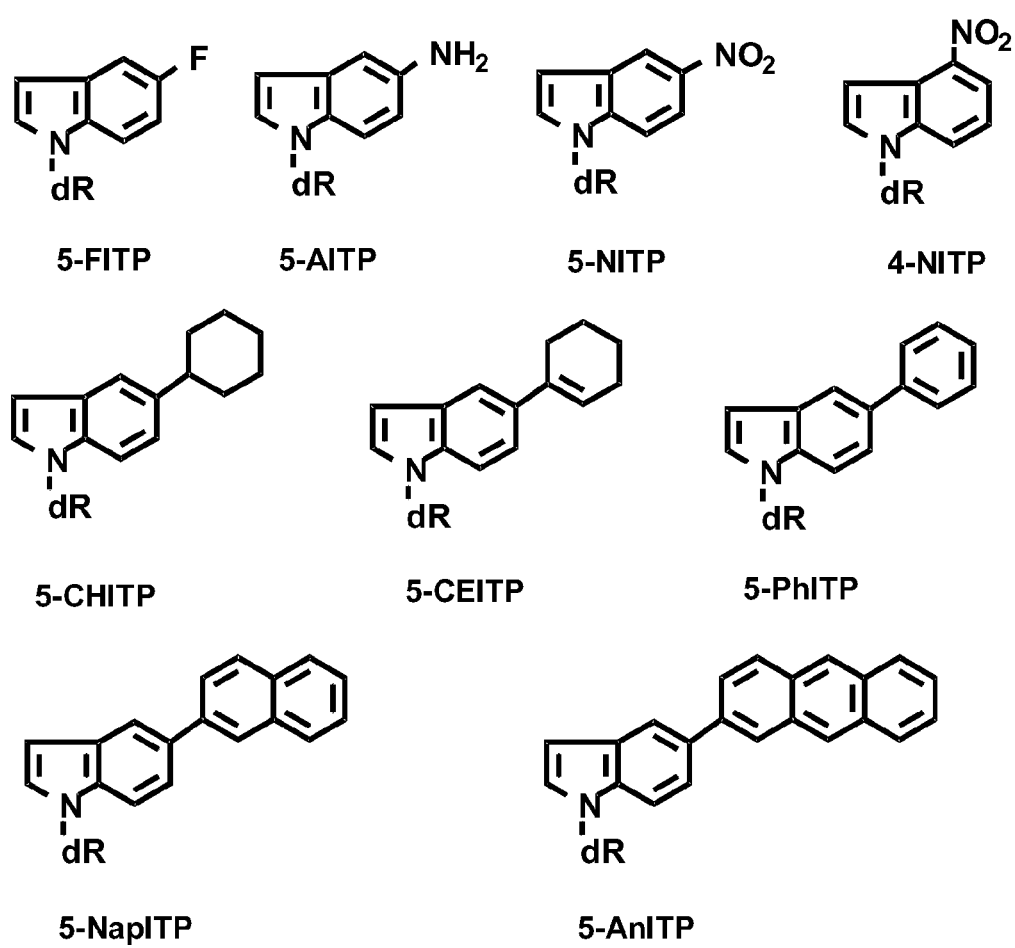
FIG. 1 illustrates a series of non-natural nucleoside analogs that mimic the core structure of adenosine.

The present invention is directed to a nucleoside analog that inhibits p-glycoprotein activity in cells. The cells can include, for example, neoplastic cells, cancerous cells, or tumorgenic cells that express p-glycoprotein, such as ovarian cancer cells, colorectal cancer cells, breast cancer cells, and acute myelogenous leukemia. The chemotherapeutic agent of the present invention can be used alone to treat a neoplastic disorder or to potentiate the cytoxic effects of other chemotherapeutics that are for example, substrates for p-glycoprotein.

In another aspect, the nucleoside analog of the present invention can also attack multiple targets associated with cancer progression, which can alleviate the disadvantages of multi-drug regimens. By attacking or hitting multiple targets, the nucleoside analog of the present invention optimizes maximal neoplastic cell kill with effectiveness against a broad range of cancer cell populations.

The nucleoside analog in accordance with the present invention can comprise an adenine deoxyribose analog having the formula (I):

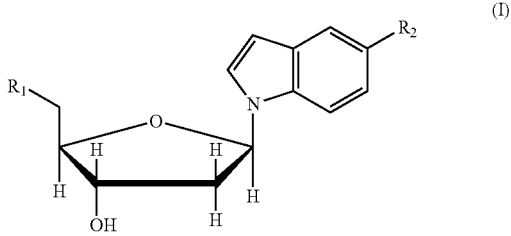

(I)

where $R_1$ is OH, monophosphate ($H_2O_3PO$— or ($O_3PO$—$)^{2-}$), diphosphate ($H_3(O_3PO)_2$— or (($O_3PO)_2$—$)^{3-}$), triphosphate ($H_4(O_3PO)_3$—, (($O_3PO)_3$—$)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative; and where $R_2$ is an unsubstituted or substituted cyclohexyl; a pharmaceutically acceptable salt thereof; or a prodrug thereof.

The phrase "having the formula" or "having the structure" is not intended to be limiting and is used in the same way that the term "comprising" is commonly used.

By "substituted" it is meant with respect to the cyclohexyl moiety moiety, at least one hydrogen atom bound to a carbon (or other) atom is replaced with one or more non-hydrogen substituents. Examples of such substituents include, without limitation: functional groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano(—CN), isocyano (—$N^+C^-$), cyanato (—O—CN), isocyanato (—$ON^+C^-$), isothiocyanato (—S—CN), azido (—N=$N^+$=$N^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)($O^-$)$_2$), phosphinato (—P(O)($O^-$)), phospho (—$PO_2$), and phosphino (—$PH_2$); and the hydrocarbyl moieties $C_1$-$C_{24}$ alkyl (preferably $C_1$-$C_{18}$ alkyl, more preferably $C_1$-$C_{12}$ alkyl, most preferably $C_1$-$C_6$ alkyl), $C_2$-$C_{24}$ alkenyl (preferably $C_2$-$C_{18}$ alkenyl, more preferably $C_2$-$C_{12}$ alkenyl, most preferably $C_2$-$C_6$ alkenyl), $C_2$-$C_{24}$ alkynyl (preferably $C_2$-$C_{18}$ alkynyl, more preferably $C_2$-$C_{12}$ alkynyl, most preferably $C_2$-$C_6$ alkynyl), $C_5$-$C_{20}$ aryl (preferably $C_5$-$C_{14}$ aryl), $C_6$-$C_{24}$ alkaryl (preferably $C_6$-$C_{18}$ alkaryl), and $C_6$-$C_{24}$ aralkyl (preferably $C_6$-$C_{18}$ aralkyl).

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When referring to a compound of the invention, applicants intend the term "compound" to encompass not only the specified molecular entity but also its pharmaceutically acceptable, pharmacologically active analogs, including, but not limited to, salts, esters, amides, prodrugs, conjugates, active metabolites, and other such derivatives, analogs, and related compounds.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" derivative or analog, refers to a derivative or analog having the same type of pharmacological activity as the parent compound and approximately equivalent in degree.

As used herein, the term "pharmaceutically acceptable salts" or complexes refers to salts or complexes of the nucleosides that retain the desired biological activity of the parent compound and exhibit minimal, if any, undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acids, naphthalenedisulfonic acids, and polygalacturonic acid; (b) base addition salts formed with cations such as sodium, potassium, zinc, calcium, bismuth, barium, magnesium, aluminum, copper, cobalt, nickel, cadmium, sodium, potassium, and the like, or with an organic cation formed from N,N-dibenzylethylene-diamine, ammonium, or ethylenediamine; or (c) combinations of (a) and (b); e.g., a zinc tannate salt or the like.

The term "prodrug", as used herein, refers to a compound that is converted into the nucleoside on administration in vivo. Nonlimiting examples are pharmaceutically acceptable salts (alternatively referred to as "physiologically acceptable salts"), the 5'-acylated or alkylated derivatives of the active compound, and the 5'-phospholipid and 5'-ether lipid derivatives of the active compound.

In one example, the adenine deoxyribose analog can comprise a 5-cylclohexyl-1-indolyl-2-deoxyriboside (5-CHInd) having the formula (II):

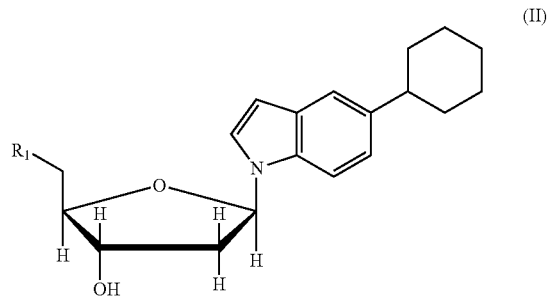

where $R_1$ is OH, monophosphate ($H_2O_3PO-$ or ($O_3PO-)^{2-}$), diphosphate ($H_3(O_3PO)_2-$ or $((O_3PO)_2-)^{3-}$), triphosphate ($H_4(O_3PO)_3-$, $((O_3PO)_3-)^{4-}$), or $OR_a$, where $R_a$ comprises at least one of a straight chain, branched or cylclic alkyl, CO-alkyl, CO-aryl, CO-alkoxyalkyl, arylsulfonyl, aralkylsulfonyl, amino acid residude, fatty acid residue, or a mono, di, or triphosphate derivative; a pharmaceutically acceptable salt thereof; or a prodrug thereof.

The indolyl deoxyribose analog can be prepared by various synthetic methods. By way of example, 5-$R_2$-indolyl-2'deoxyriboside can be prepared by reacting a riboside with 5-$R_2$-indole as shown in the following reaction scheme:

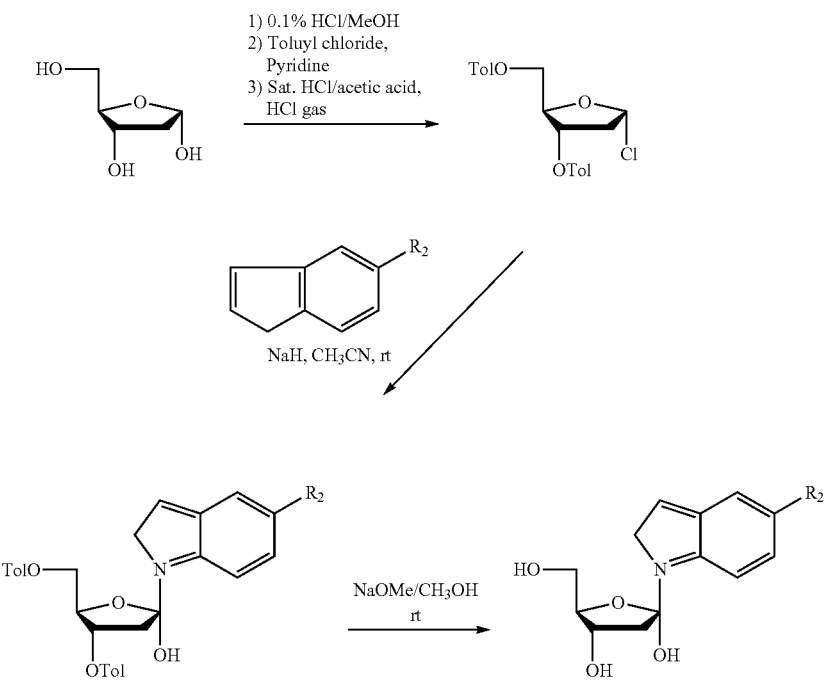

In this example, the riboside can be initially mixed and reacted in a first reaction with (1) HCl/MeOH, (2) toluoyl chloride, pyridine (3) saturated HCl/acetic acid and HCl gas to form 1-chloro-3,5-di-O-toluoyl-2-deoxyriboside. The 1-chloro-3,5-di-O-toluoyl-2-deoxyriboside can then be reacted with 5-$R_2$-indole (e.g., 5-cyclohexyl-indole) and NaOMe/Methanol, at room temperature to form 5-$R_2$-indolyl-2'deoxyriboside.

The adenine deoxyriboside analogs of formulas (I-II) can be used as therapeutic agents for the treatment of a disorder, such as a neoplastic disorder, for example, ovarian cancer, colorectal cancer, breast cancer, and acute myelogenous leukemia. When used as therapeutic agents, the adenine deoxyriboside analogs of formulas (I-II) can be conveniently formulated into pharmaceutical formulations composed of one or more of the compounds (i.e., adenine deoxyriboside analogs of formulas (I-II)) in association with a pharmaceutically acceptable carrier. (See Remington: The Science and Practice of Pharmacy, 19.sup.th Ed. (Easton, Pa.: Mack Publishing Co., 1995), which discloses typical carriers and conventional methods of preparing pharmaceutical formulations.)

The term "treatment" refers to reduction in severity and/or frequency of symptoms, elimination of symptoms and/or underlying cause, prevention of the occurrence of symptoms and/or their underlying cause, and improvement or remediation of damage. For example, treatment of a patient by administration of a compound (e.g., nucleoside analog) of the invention encompasses chemoprevention in a patient susceptible to developing cancer (e.g., at a higher risk, as a result of genetic predisposition, environmental factors, or the like) and/or in cancer survivors at risk of cancer recurrence, as well as treatment of a cancer patient by inhibiting or causing regression of a disorder or disease.

The adenine deoxyriboside analogs of formulas (I-II) can also be administered as a stabilized nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, Antiviral Research, 27 (1995) 1-17. Any of these can be used in combination with the disclosed nucleosides to achieve a desired effect.

In one aspect of the invention, the adenine deoxyriboside analogs of formula (I-II) can be provided as a 5'-hydroxyl lipophilic prodrug. Nonlimiting examples of U.S. patents that disclose suitable lipophilic substituents that can be covalently incorporated into the nucleoside, at the 5'-OH position of the nucleoside or lipophilic preparations, include U.S. Pat. No. 5,149,794; U.S. Pat. No. 5,194,654, U.S. Pat. No. 5,223,263; U.S. Pat. No. 5,256,641; U.S. Pat. No. 5,411,947; U.S. Pat. No. 5,463,092; U.S. Pat. No. 5,543,389; U.S. Pat. No. 5,543,390; U.S. Pat. No. 5,543,391; and U.S. Pat. No. 5,554,728, all of which are incorporated herein by reference.

The adenine deoxyribose analogs of formulas (I-II) may be administered orally, parenterally, rectally, vaginally, buccally, sublingually, nasally, by inhalation, topically, transdermally, or via an implanted reservoir in dosage forms containing conventional non-toxic pharmaceutically acceptable carriers and excipients. The term "parenteral" as used herein is intended to include subcutaneous, intravenous, and intramuscular injection. The amount of the adenine deoxyriboside analogs of formulas (I-II) administered can, of course, be a therapeutically effective amount and can be dependent on the particular active agent, the condition or disorder being treated, the severity of the condition or disorder, the subject's weight, the mode of administration and other pertinent factors known to the prescribing physician. Generally, however, dosage can be in the range of approximately 0.001 μg/mL/day to 100 μg/mL/day, more preferably in the range of about 0.1 μg/mL/day to 10 μg/ml/day.

Depending on the intended mode of administration, the pharmaceutical formulation may be a solid, semi-solid or liquid, such as, for example, a tablet, a capsule, caplets, a liquid, a suspension, an emulsion, a suppository, granules, pellets, beads, a powder, or the like, preferably in unit dosage form suitable for single administration of a precise dosage. Pharmaceutical compositions and dosage forms may be prepared using conventional methods known to those in the field of pharmaceutical formulation and described in the pertinent texts and literature, e.g., in Remington: The Science and Practice of Pharmacy, cited above.

For those compounds that are orally active, oral dosage forms are generally preferred, and include tablets, capsules, caplets, solutions, suspensions and syrups, and may also comprise a plurality of granules, beads, powders or pellets that may or may not be encapsulated. Preferred oral dosage forms are tablets and capsules.

Tablets may be manufactured using standard tablet processing procedures and equipment. Direct compression and granulation techniques are preferred. In addition to the active agent, tablets can generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose, and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, Remington: The Science and Practice of Pharmacy, cited supra, which describes materials and methods for preparing encapsulated pharmaceuticals.

Oral dosage forms, whether tablets, capsules, caplets, or particulates, may, if desired, be formulated so as to provide for gradual, sustained release of the active agent over an extended time period. Generally, as will be appreciated by those of ordinary skill in the art, sustained release dosage forms are formulated by dispersing the active agent within a matrix of a gradually hydrolyzable material such as an insoluble plastic (e.g., polyvinyl chloride or polyethylene), or a hydrophilic polymer, or by coating a solid, drug-containing dosage form with such a material. Hydrophilic polymers useful for providing a sustained release coating or matrix include, by way of example: cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone, polyvinyl acetate, and ethylene-vinyl acetate copolymer.

Preparations according to this invention for parenteral administration include sterile nonaqueous solutions, suspensions, and emulsions. Examples of nonaqueous solvents or vehicles are propylene glycol, polyethylene glycol, vegetable oils, such as olive oil and corn oil, gelatin, and injectable organic esters such as ethyl oleate. Parenteral formulations may also contain adjuvants such as preserving, wetting, emulsifying, and dispersing agents. The formulations are rendered sterile by incorporation of a sterilizing agent, filtration through a bacteria-retaining filter, irradiation, or heat. They can also be manufactured using a sterile injectable medium.

The compounds of the invention may also be administered through the skin or mucosal tissue using conventional transdermal drug delivery systems, wherein the active agent is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. Transdermal drug delivery systems may in addition contain a skin permeation enhancer.

Although the present compounds can generally be administered orally, parenterally, or transdermally, other modes of administration are suitable as well. For example, administration may be rectal or vaginal, preferably using a suppository that contains, in addition to the active agent, excipients such cocoa butter or a suppository wax. Formulations for nasal or sublingual administration are also prepared with standard excipients well known in the art. The pharmaceutical compositions of the invention may also be formulated for inhalation, e.g., as a solution in saline, as a dry powder, or as an aerosol.

The adenine deoxyribose analogs of formulas (I-II) are of value in a number of methods. In one method, the adenine deoxyriboside analogs of formulas (I-II) can be administered to a cell expressing a P-glycoprotein in vivo in a mammal (or in vitro) to inhibit the activity of P-glycoprotein, a transmembrane enzyme associated with multi drug resistance. P-glycoprotein (P-gp) is known to export various chemotherapeutic agents such as vinblastine, doxorobucin, and paclitaxel out of a cancer cell. P-gp is frequently over-expressed in many cancers and confers drug resistance by decreasing the intracellular concentration of chemotherapeutic agents. Representative flow cytometry data provided in (FIG. 2B), shows the rapid cytotoxic effect caused by 5-CHInd that closely mimics that of staurosporine, an inhibitor of CDK1, CDK2, and CDK5. 5-CHInd is among the series of non-natural nucleoside analogs that mimic the core structure of adenosine (FIG. 1). Although all of the non-natural nucleosides induce apoptosis (FIG. 4), 5-CHInd is unique in that it alone can inhibit the activity of P-gp.

The adenine deoxyriboside analogs of formulas (I-II) can also induce cell death by inhibiting cyclin dependent kinases. Uncontrolled proliferation occurs through dysfunctional cell cycle regulation and checkpoint controls that are caused by aberrant CDK activity; thus targeting the activity of one or more CDKs provides a clear therapeutic strategy to treat proliferative diseases, such as neoplastic disorders. CDKs are essential for the highly poliferative nature of most cancers.

Furthermore, adenine deoxyriboside analogs of formulas (I-II) can inhibit or block binding of ATP to CDK enzymes and P-gp. P-gp utilizes ATP hydrolysis to actively transport drugs such as vinblastine and doxorobucin out of a cancer cell to render them therapeutically ineffective. Adenine deoxyriboside analogs of formulas (I-II) can block ATP binding to CDKs and P-gp to inhibit the ability of CDKs to phosphorylate proteins needed for cell-cycle progression and mitigate cancer growth and prevent the transport of chemotherapeutic agents by P-gp to thwart drug resistance.

In another aspect of the invention, a method of inhibiting multiple chemotherapeutic targets using a singular molecular agent includes administering the therapeutic agent 5-Cyclohexyl-Indole-Nucleoside (5-CHInd) to a subject.

In yet another aspect of the invention, a method of inhibiting multiple drug resistance in neoplastic cells includes administering a pharmaceutical composite that includes a 5-Cyclohexyl-Indole-Nucleoside (5-CHInd).

In a further aspect of the invention, the adenine deoxyribose analogs of formulas (I-II) can be used in combination and adjunctive therapies for treating mammalian diseases, such as in therapies for neoplastic disorders in which P-glycoprotein substrates are administered to treat the disease.

The phrase "combination therapy" embraces the administration of the adenine deoxyribose analogs of formulas (I-II), and a therapeutic agent as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected). "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

The phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The mammalian disease treated by the combination therapy can include proliferative diseases, such as neoplastic disorders (e.g., ovarian cancer, colorectal cancer, breast cancer, and acute myeloid leukemia) and autoimmune dysfunctions as well as viral and microbial infections. Besides being useful for human treatment, the combination therapy is also useful for veterinary treatment of companion animals, exotic and farm animals, including rodents, horses, dogs, and cats.

In an aspect of the invention, the therapeutic agent administered in combination therapy with the adenine deoxyribose analogs of formulas (I-II) can comprise cytoxic or chemotherapeutic agents. The cytotoxic agents or chemotherapeutic agents can be, for example, P-glycoprotein drug substrates, such as weak bases and hydrophobic molecules. The adenine deoxyribose analogs of formulas (I-II) can potentiate the cytotoxic effect of the chemotherapeutic agents that are substrates to P-gp on multiple drug resistant neoplastic cells.

In another aspect of the invention, the therapeutic agents administered in combination therapy with the adenine deoxyribose analogs of formulas (I-II) can comprise at least one anti-proliferative agent selected from the group consisting of a chemotherapeutic agent, an antimetabolite, an antitumorgenic agent, an antimitotic agent, an antiviral agent, an antineoplastic agent, an immunotherapeutic agent, and a radiotherapeutic agent.

The phrase "anti-proliferative agent" can include agents that exert antineoplastic, chmotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development, which could be included in the present invention by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endotheliai cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

A first family of anti-proliferative agents, which may be used in combination therapy with the adenine deoxyribose analog of formula (I-II) consists of antimetabolite-type anti-proliferative agents. Antimetabolites are typically reversible or irreversible enzyme inhibitors, or compounds that otherwise interfere with the replication, translation or transcription of nucleic acids. Examples of antimetabolite antineoplastic agents that may be used in the present invention include, but are not limited to acanthifolic acid, aminothiadiazole, anastrozole, bicalutamide, brequinar sodium, capecitabine, carmofur, Ciba-Geigy CGP-30694, cladribine, cyclopentyl cytosine, cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, finasteride, floxuridine, fludarabine phosphate, N-(2'-furanidyl)-5-fluorouracil, Daiichi Seiyaku FO-152, fluorouracil (5-FU), 5-FU-fibrinogen, isopropyl pyrrolizine, Lilly LY-188011, Lilly LY-264618, methobenzaprim, methotrexate, Wellcome MZPES, nafarelin, norspermidine, nolvadex, NCI NSC-127716, NCI NSC-264880, NCI NSC-39661, NCI NSC-612567, Warner-Lambert PALA, pentostatin, piritrexim, plicamycin, Asahi Chemical PL-AC, stearate; Takeda TAC-788, thioguanine, tiazofurin, Erbamont TIF, trimetrexate, tyrosine kinase inhibitors, tyrosine protein kinase inhibitors, Taiho UFT, toremifene, and uricytin, all of which are disclosed in U.S. Pat. No. 6,916,800, which is herein incorporated by reference in its entirety.

A second family of anti-proliferative agents, which may be used in combination therapy with the analogs of the present invention consists of alkylating-type anti-proliferative agents. The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. A disadvantage with these compounds is that they not only attack malignant cells, but also other cells which are naturally dividing, such as those of bone marrow, skin, gastro-intestinal mucosa, and fetal tissue. Examples of alkylating-type anti-proliferative agents that may be used in the present invention include, but are not limited to, Shionogi 254-S, aldo-phosphamide analogues, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, etoposide phosphate, fotemustine, Unimed G-6-M, Chinoin GYKI-17230, hepsulfam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromus-tine, Tanabe Seiyaku TA-077, tauromustine, temozolomide, teroxirone, tetraplatin and trimelamol.

A third family of anti-proliferative agents that may be used in combination therapy with the analogs of the present invention consists of antibiotic-type anti-proliferative agents. Examples of antibiotic-type anti-proliferative agents that may be used in the present invention include, but are not limited to Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of anti-proliferative agents that may be used in combination therapy with the anaologs of the present invention consists of synthetic nucleosides. Several synthetic nucleosides have been identified that exhibit anticancer activity. A well known nucleoside derivative with strong anticancer activity is 5-fluorouracil (5-FU). 5-Fluorouracil has been used clinically in the treatment of malignant tumors, including, for example, carcinomas, sarcomas, skin cancer, cancer of the digestive organs, and breast cancer. 5-Fluorouracil, however, causes serious adverse reactions such as nausea, alopecia, diarrhea, stomatitis, leukocytic thrombocytopenia, anorexia, pigmentation, and edema. Derivatives of 5-fluorouracil with anti-cancer activity have been described in U.S. Pat. No. 4,336,381, which is herein incorporated by reference in its entirety.

A fifth family of anti-proliferative agents that may be used in combination therapy with the analogs of the present invention consists of hormonal agents. Examples of hormonal-type anti-proliferative agents that may be used in the present invention include, but are not limited to Abarelix; Abbott A-84861; Abiraterone acetate; Aminoglutethimide; anastrozole; Asta Medica AN-207; Antide; Chugai AG-041R; Avorelin; aseranox; Sensus B2036-PEG; Bicalutamide; buserelin; BTG CB-7598; BTG CB-7630; Casodex; cetrolix; clastroban; clodronate disodium; Cosudex; Rotta Research CR-1505; cytadren; crinone; deslorelin; droloxifene; dutasteride; Elimina; Laval University EM-800; Laval University EM-652; epitiostanol; episteride; Mediolanum EP-23904; EntreMed 2-ME; exemestane; fadrozole; finasteride; flutamide; formestane; Pharmacia & Upjohn FCE-24304; ganirelix; goserelin; Shire gonadorelin agonist; Glaxo Wellcome GW-5638; Hoechst Marion Roussel Hoe-766; NCI hCG; idoxifene; isocordoin; Zeneca ICI-182780; Zeneca ICI-118630; Tulane University J015X; Schering Ag J96; ketanserin; lanreotide; Milkhaus LDI-200; letrozol; leuprolide; leuprorelin; liarozole; lisuride hydrogen maleate; loxiglumide; mepitiostane; Leuprorelin; Ligand Pharmaceuticals LG-1127; LG-1447; LG-2293; LG-2527; LG-2716; Bone Care International LR-103; Lilly LY-326315; Lilly LY-353381-HCl; Lilly LY-326391; Lilly LY-353381; Lilly LY-357489; miproxifene phosphate; Orion Pharma MPV-2213ad; Tulane University MZ-4-71; nafarelin; nilutamide; Snow Brand NKS01; octreotide; Azko Nobel ORG-31710; Azko Nobel ORG-31806; orimeten; orimetene; orimetine; ormeloxifene; osaterone; Smithkline Beecham SKB-105657; Tokyo University OSW-1; Peptech PTL-03001; Pharmacia & Upjohn PNU-156765; quinagolide; ramorelix; Raloxifene; statin; sandostatin LAR; Shionogi S-10364; Novartis SMT-487; somavert; somatostatin; tamoxifen; tamoxifen methiodide; teverelix; toremifene; triptorelin; TT-232; vapreotide; vorozole; Yamanouchi YM-116; Yamanouchi YM-511; Yamanouchi YM-55208; Yamanouchi YM-53789; Schering AG ZK-1911703; Schering AG ZK-230211; and Zeneca ZD-182780.

A sixth family of anti-proliferative agents that may be used in combination therapy with the anaologs of the present invention consists of a miscellaneous family of antineoplastic agents including, but not limited to alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristo-Myers BMY-40481, Vestar boron-10, bromofosfamide, Wellcome BW-502, Wellcome BW-773, calcium carbonate, Calcet, Calci-Chew, Calci-Mix, Roxane calcium carbonate tablets, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Cell Pathways CP-461, Yakult Honsha CPT-11, crisnatol, curaderm, cytochalasin B, cytarabine, cytocytin, Merz D-609, DABIS maleate, dacarbazine, datelliptinium, DFMO, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel, Encore Pharmaceuticals E7869, elliprabin, elliptinium acetate, Tsumura EPMTC, ergotamine, etoposide, etretinate, Eulexin®, Cell Pathways Exisulind® (sulindac sulphone or CP-246), fenretinide, Merck Research Labs Finasteride, Florical, Fujisawa FR-57704, gallium nitrate, gemcitabine, genkwadaphnin, Gerimed, Chugai GLA-43, Glaxo GR-63178, grifolan NMF-5N, hexadecylphosphocholine, Green Cross HO-221, homoharringtonine, hydroxyurea, BTG ICRF-187, ilmofosine, irinotecan, isoglutamine, isotretinoin, Otsuka JI-36, Ramot K-477, ketoconazole, Otsuak K-76COONa, Kureha Chemical K-AM, MECT Corp KI-8110, American Cyanamid L-623, leucovorin, levamisole, leukoregulin, lonidamine, Lundbeck LU-23-112, Lilly LY-186641, Materna, NCI (US) MAP, marycin, Merrel Dow MDL-27048, Medco MEDR-340, megestrol, merbarone, merocyanine derivatives, methylanilinoacridine, Molecular Genetics MGI-136, minactivin, mitonafide, mitoquidone, Monocal, mopidamol, motretinide, Zenyaku Kogyo MST-16, Mylanta, N-(retinoyl)amino acids, Nilandron; Nisshin Flour Milling N-021, N-acylated-dehydroalanines, nafazatrom, Taisho NCU-190, Nephro-Calci tablets, nocodazole derivative, Normosang, NCI NSC-145813, NCI NSC-361456, NCI NSC-604782, NCI NSC-95580, octreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, retinoids, Encore Pharmaceuticals R-flurbiprofen, Sandostatin; Sapporo Breweries RBS, restrictin-P, retelliptine, retinoic acid, Rhone-Poulenc RP-49532, Rhone-Poulenc RP-56976, Scherring-Plough SC-57050, Scherring-Plough SC-57068, seienium(selenite and selenomethionine), SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, Sugen SU-101, Sugen SU-5416, Sugen SU-6668, sulindac, sulindac sulfone; superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine, vinblastine sulfate, vincristine, vindesine, vinestramide, vinorelbine, vintriptol, vinzolidine, withanolides, Yamanouchi YM-534, Zileuton, ursodeoxycholic acid, and Zanosar.

In a further aspect of the invention, the therapeutic agent administered in combination therapy with the adenine deoxyribose analogs of formula (I-II) can comprise P-glycoprotein drug substrates, weak bases and hydrophobic molecules, including chemotherapeutic agents, such as vinca alkyloids, anthracyclines, taxanes, epiodophyllotoxins, and antibiotcis. Specific examples of such P-glycoprotein drug substrates include acetolol, amiodarone, atorvastatin, celiprolol, cimetidine, ciprofloxacin, colchicines, cyclosporine, daunorubicin, debrisoquine, DHEA, digoxin, diltiazem, docetaxel, domperidone, doxorubicin, enoxacin, erythromycin, estradiol, etoposide, fexofenadine, hydrocortisone, idarubicin, indinavir, ivermectin, lidocaine, loperamide, methotrexate, mibefradil, nadalol, nelfinavir, nicardipine, ondansetron, paclitaxel, pravastatin, quinidine, quinolones, rantidine, rifampin, ritonavir, saquinaivr, tacrolilmus, taxol, teniposide, terfenadine, timolol, verapamil, vinblastine, vinicristin, vindesine and combinations thereof.

The foregoing treatment methods and uses can generally involve the administration of a pharmaceutically effective composition of the adenine deoxyribose analogs of formulas (I-II) to the animal or patient systemically, such as by transdermal, intramuscular, intravenous injection and the like. However, any route of administration that allows the therapeutic agent to localize to the site or sites of the cells, which are being treated by the DNA damaging agent can be acceptable. Therefore, other suitable routes of delivery include oral, rectal, nasal, topical, and vaginal. U.S. Pat. No. 5,712,291, is incorporated herein by reference for purposes including further describing the various routes of administration that may be included in connection with the treatment of an angiogenic disease or disorder. For conditions associated with the eye, ophthalmic formulations and administration are contemplated.

"Administration", as used herein, means provision or delivery of the adenine deoxyribose analogs of formula (I) therapeutic agents in an amount(s) and for a period of time(s) effective to inhibit translesion DNA synthesis.

The "therapeutically effective amounts" for use in the invention are amounts adenine deoxyribose analogs of formula (I-II) effective to inhibit translesion DNA synthesis and to potentiate the cytotoxic effects of the DNA damaging agent. Such effects are achieved without substantially inhibiting normal DNA synthesis in normal, healthy cells or tissues; and exerting negligible or manageable adverse side effects on normal, healthy cell or tissues of the animal or patient.

The adenine deoxyribose analogs of formula (I-II) in accordance with the present invention can allow the combination therapeutic agents and therapies of the present invention to be administered at a low dose, that is, at a dose lower than has been conventionally used in clinical situations.

A benefit of lowering the dose of the combination therapeutic agents and therapies of the present invention administered to a mammal includes a decrease in the incidence of adverse effects associated with higher dosages. For example, by the lowering the dosage of a chemotherapeutic agent such as methotrexate, a reduction in the frequency and the severity of nausea and vomiting will result when compared to that observed at higher dosages. Similar benefits are contemplated for the compounds, compositions, agents and therapies in combination with the inhibitors of the present invention.

By lowering the incidence of adverse effects, an improvement in the quality of life of a patient undergoing treatment for cancer is contemplated. Further benefits of lowering the incidence of adverse effects include an improvement in patient compliance, a reduction in the number of hospitalizations needed for the treatment of adverse effects, and a reduction in the administration of analgesic agents needed to treat pain associated with the adverse effects.

Alternatively, the methods and combination of the present invention can also maximize the therapeutic effect at higher doses.

When administered as a combination, the therapeutic agents can be formulated as separate compositions which are given at the same time or different times, or the therapeutic agents can be given as a single composition.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example

We probed the non-natural nucleotide library for potential lead compounds (FIG. 1). These analogs were tested for cytotoxic effects against various cancer cell lines including CEM/VBL and SKOV/VBL which display multi-drug resistance due to overexpression of p-glycoprotein.

Figure 2A:
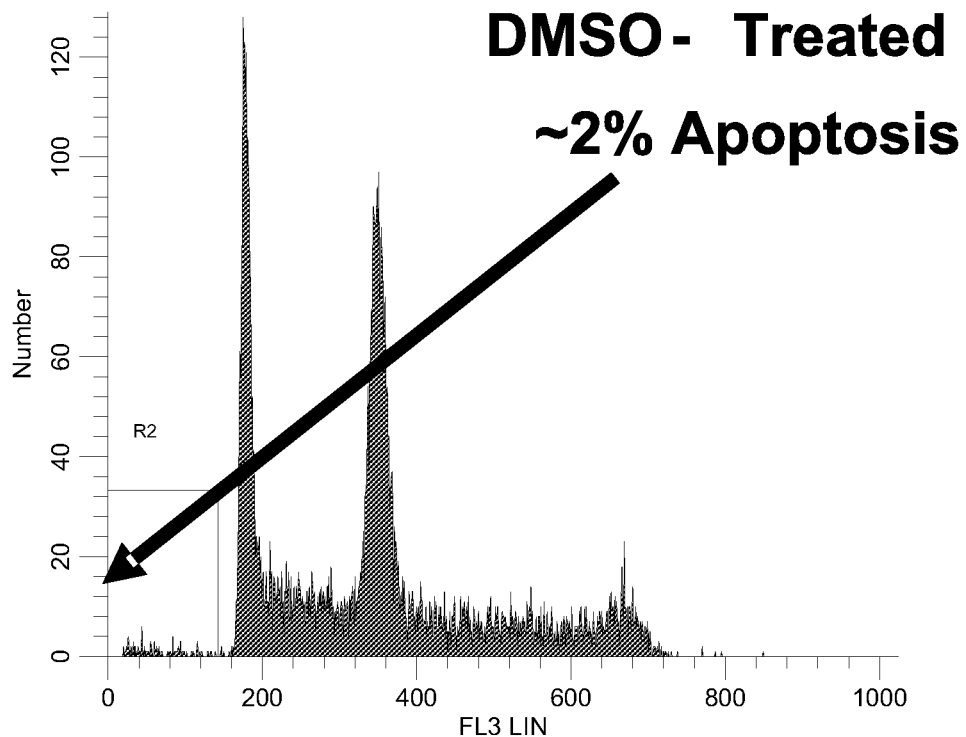
FIG. 2 illustrates representative flow cytometry data showing a rapid cytotoxic effect caused by 5-CHInd that closely mimics that of staurosporine, an inhibitor of CDK1, CDK2, and CDK5. Nucleoside analogs were tested for cytotoxic effects against a variety of leukemia cell lines including CEM-VBL which displays multi-drug resistance due to over-expression of P-gp.
Figure 2B:
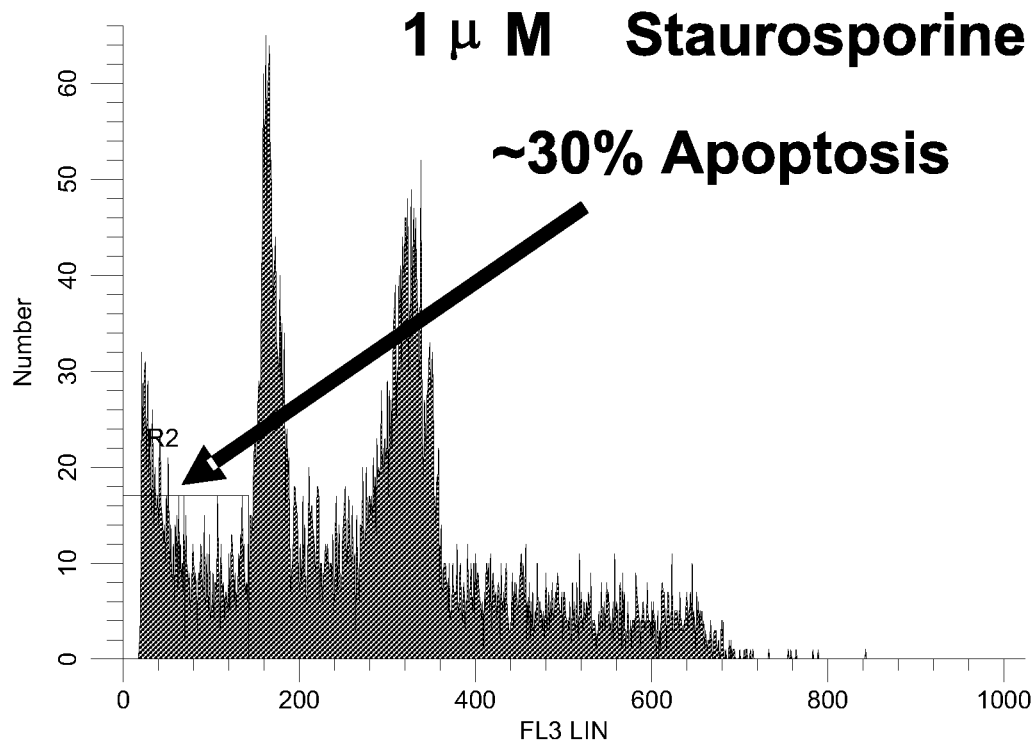
Figure 2C:
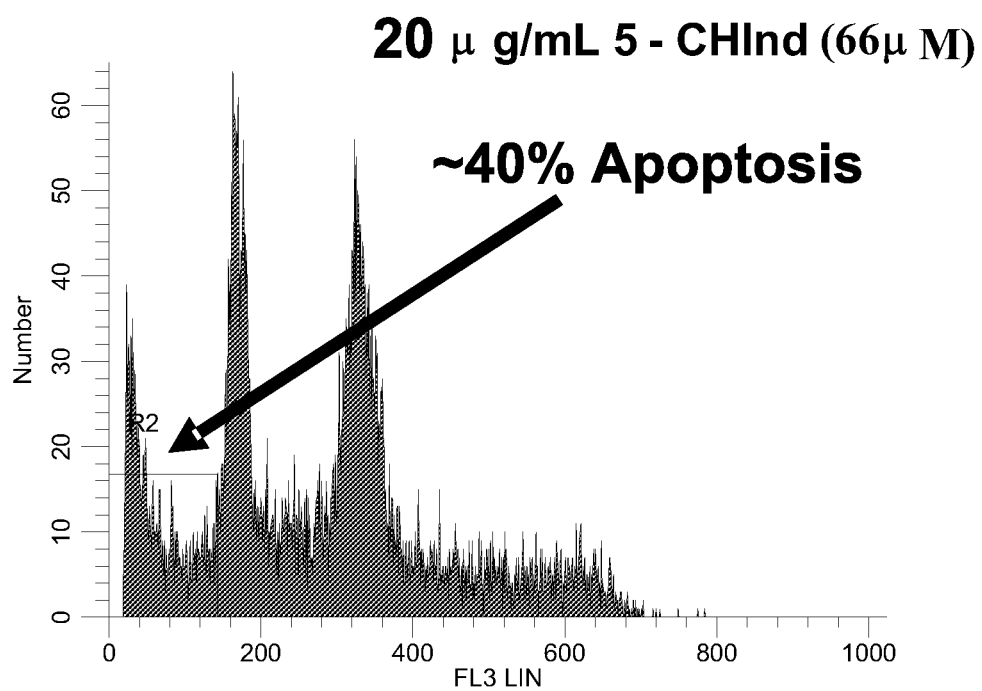

Representative flow cytometry data provided in FIG. 2 shows that 5-CHInd induces a rapid cytotoxic effect in leukemia cells that closely mimics the effects of staurosporine, an inhibitor of CDK1, CDK2, and CDK5. Other non-natural nucleosides such as 5-PhInd and 5-NapInd also cause cell death at the concentrations tested (data not shown). However, 5-CHInd is the most potent of these analogs, possessing an $LD_{50}$ value of about 20 µg/mL against several leukemia cell lines (data not shown).

5-CHInd Blocks Drug Transport by the P-Glycoprotein.

Figure 3:
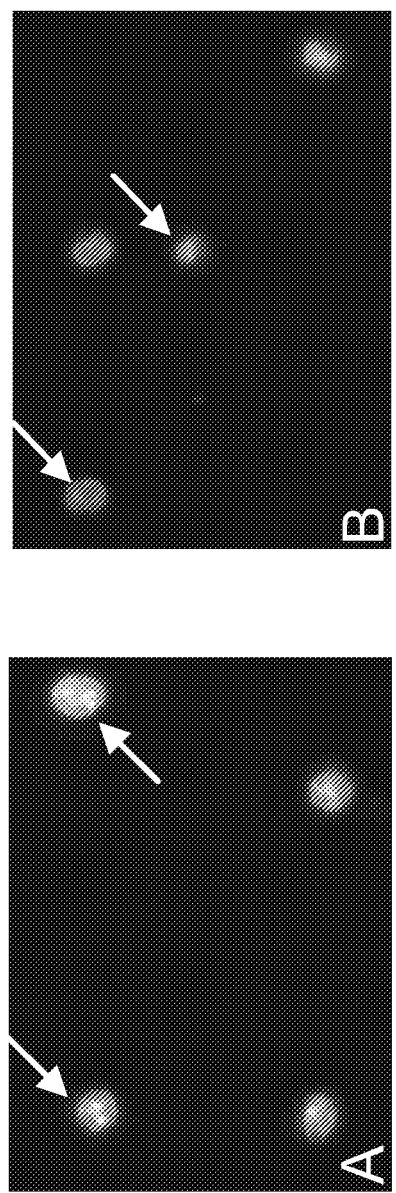
FIG. 3 illustrates microphotographs of the inhibition of P-glycoprotein by 5-CHInd leads to accumulation of Hoechst 33342 in CEM/VBL.

5-CHInd is unique since it alone can inhibit the activity of p-glycoprotein. This was first determined using the NIMH Psychoactive Drug Screening Program (PDSP) which performs pharmacological and functional screens of novel compounds. This initial screening effort lead us to test the ability of 5-CHInd to block the export of Hoechst dye, a known substrate for P-gp. Control experiments verify that CEM cells not overexpressing p-glycoprotein show accumulation of the Hoechst dye as indicated by nuclear staining (FIG. 3A). However, CEM/VBL cells overexpressing P-gp do not show a significant accumulation of the dye (FIG. 3B), suggesting that the P-gp is actively pumping the dye out of the cell. In stark contrast, CEM/VBL cells treated with a sub-lethal concentration of 5-CHInd begin to show an enhanced accumulation of the Hoechst dye (FIG. 3C) compared to untreated CEM/VBL. These results collectively suggest that 5-CHInd inhibits the activity of the P-gp. Surprisingly, no other non-natural nucleoside was able to inhibit P-gp activity (data not shown). These data lead us to hypothesize that 5-CHInd behaves as an ATP analog and targets the ATP binding pocket of P-gp.

5-CHITP Inhibits the ATPase Activity of P-gp.

Figure 4:
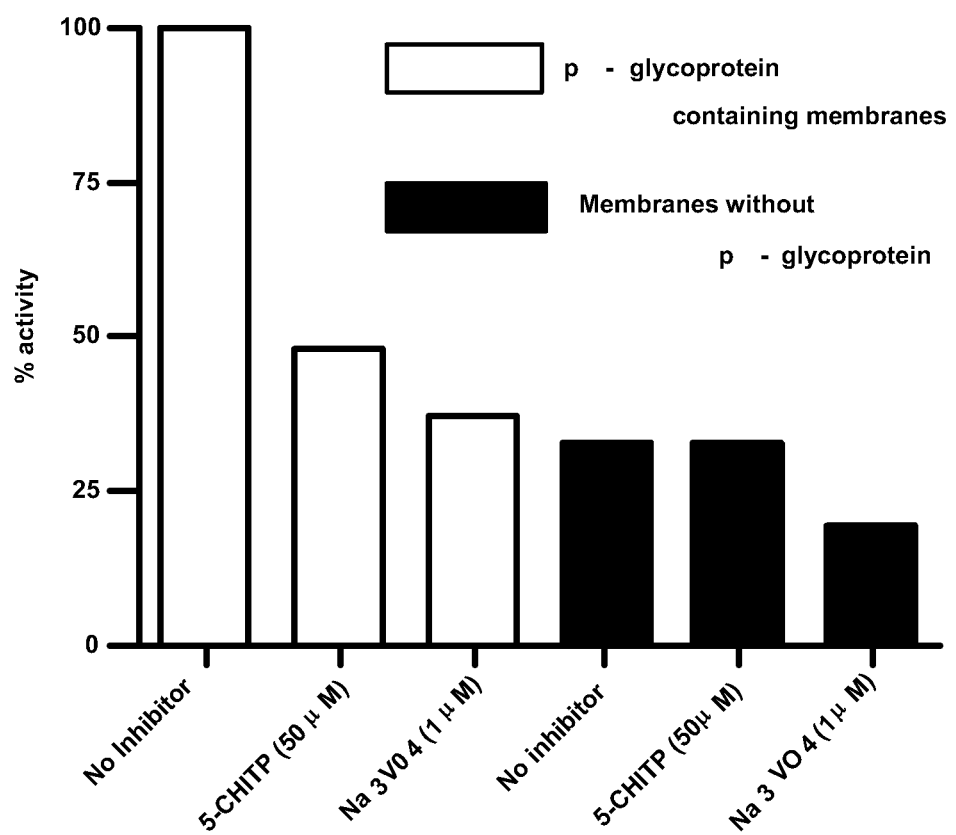
FIG. 4 illustrates a graph showing the inhibition of the ATPase activity of p-glycoprotein by 5-CHITP.

The in vitro activity of the triphosphate of 5-CHInd (5-CHITP) against P-gp was evaluated through its ability to inhibit vinblastine-stimulated ATP hydrolysis. These experiments used purified P-gp membranes expressed and isolated in Sf9 insect cells (BD Biosciences). ATP hydrolysis was quantified by the amount of $^{32}P_i$ release from $\gamma^{32}P$-ATP as a function of time. Reactions containing vinblastine were initiated by the addition of membranes and quenched in trichloroacetic acid and ammonium heptamolybdate. Heptamolybdophosphoric acid was separated by organic phase extraction and the presence of $^{32}P_i$ was quantified by liquid scintillation counting. As shown in FIG. 4, the addition of 50 µM 5-CHITP inhibits the ATPase activity of P-gp by 52% and is comparable to the inhibition displayed by 1 µM sodium orthovanadate, a potent transition-state analog inhibitor. The inhibition of 5-CHITP is selective for P-gp as the ATPase activity of control Sf9 membranes is not inhibited whereas sodium orthovanadate inhibits by about 50%.

Vinblastine and CHInd

The $LD_{50}$ value for Vinblastine is significantly higher in the MDR positive cells (CEM-VBL) as opposed to the MDR negative cell line (CEM-C7). Since vinblastine is a substrate for P-gp, the higher $LD_{50}$ value in CEM-VBL validates the activity of P-gp in mediating drug resistance. In contrast, MDR positive and negative cell lines have identical $LD_{50}$ values for 5-CHInd. We reason that 5-CHInd is an inhibitor, not a substrate for P-gp. Thus its intracellular accumulation is unaffected in either cell line such that 5-CHInd will inhibit CDKs associated with cell cycle pregression. Inhibition of CDKs will cause cell death independent of P-gp.

As an additional positive control, the $LD_{50}$ value for staurosporine was measured. Staurosporine is a known inhibitor of CDKs 1, 2, and 5. The rationale for using staurosporine is that it allows direct comparison of phenotypical responses to kinase inhibitors. Furthermore, since staurosporine is not a substrate for P-gp, its $LD_{50}$ value should be identical in both cell lines. However, staurosporine differs from 5-CHInd since it does not inhibit P-gp. Thus, staurosporine does not act as a potentiating agent.

Potentiation of Vinblastine by 5-CHInd.

Figure 5:
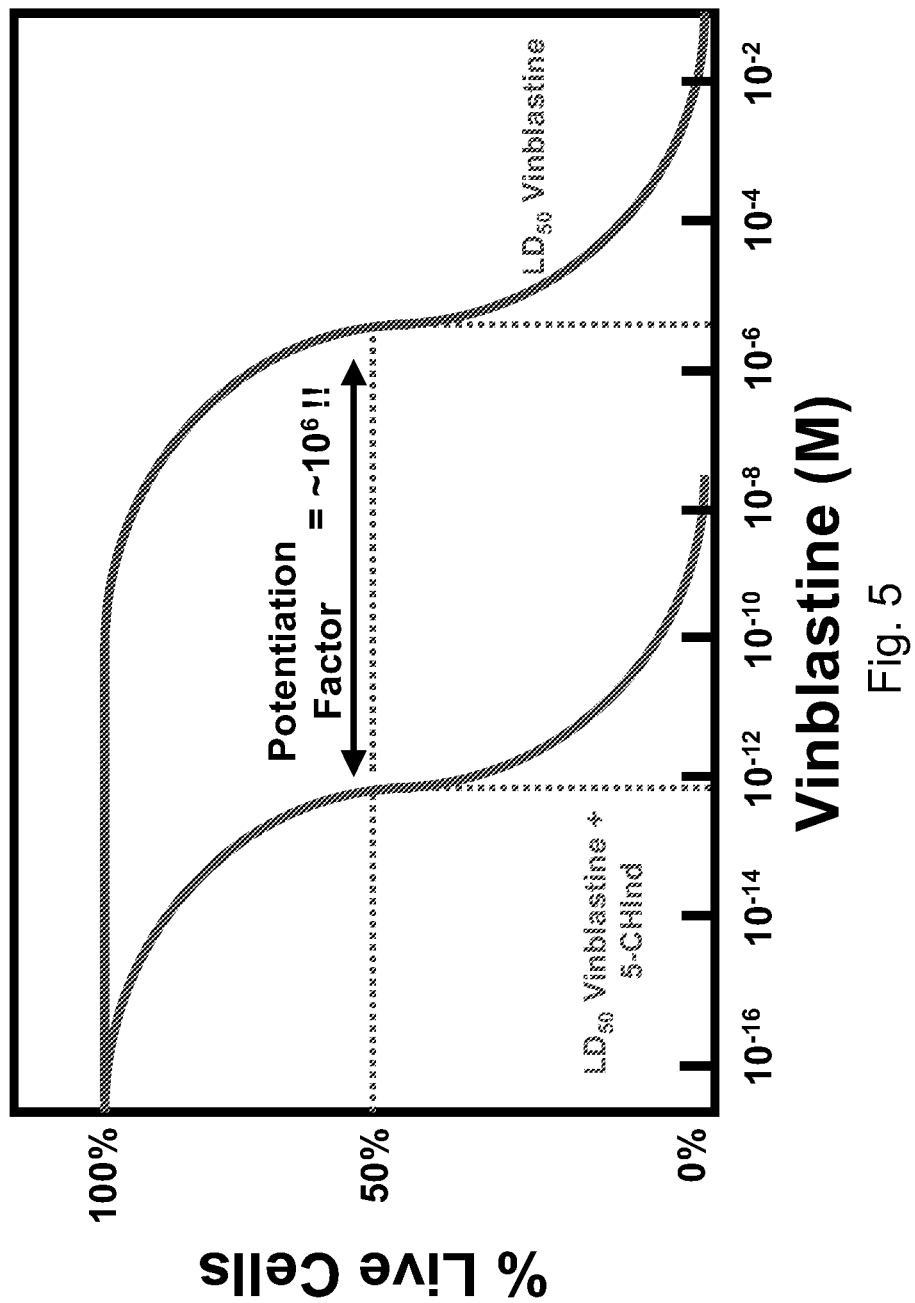
FIG. 5 illustrates a plot of the potentiating effect of 5-CHInd expressed as the ratio of $LD_{50}$ values for vinblastine measured in the absence and presence of 5-CHInd.

5-CHInd inhibits P-glycoprotein activity to reverse the causes of the MDR phenotype exhibited by the leukemia cell line (CEM-VBL). Accordingly, 5-CHInd potentiates the effects of chemotherapeutic agents that are substrates for P-glycoprotein. This was illustrated by measuring the ability of a sub-lethal dose of 5-CHInd to potentiate the cytotoxic effects of vinblastine. Cells were pretreated with a concentration of 5-CHInd for two hours prior to administering varying concentrations of vinblastine (0-500 µM). Cell viability was assessed. The potentiating effect of 5-CHInd is expressed as the ratio of $LD_{50}$ values for vinblastine measured in the absence of and presence of 5-CHInd (FIG. 5). In the absence 5-CHInd, the $LD_{50}$ for vinblastine is high since P-gp effectively transports the drug from the cell. However, a sub-lethal dose of 5-CHInd shifts the dose-dependency for vinblastine and yields a lower $LD_{50}$ value. Lowering the $LD_{50}$ value for vinblastine clearly indicates potentiation. Potentiation presumably reflects the intracellular accumulation of vinblastine that occurs through inhibition of P-gp by 5-CHInd. The physiological importance of potentiation is that lower therapeutic doses of vinblastine can be administered to reduce the risk of potential side effects.

Figure 6:
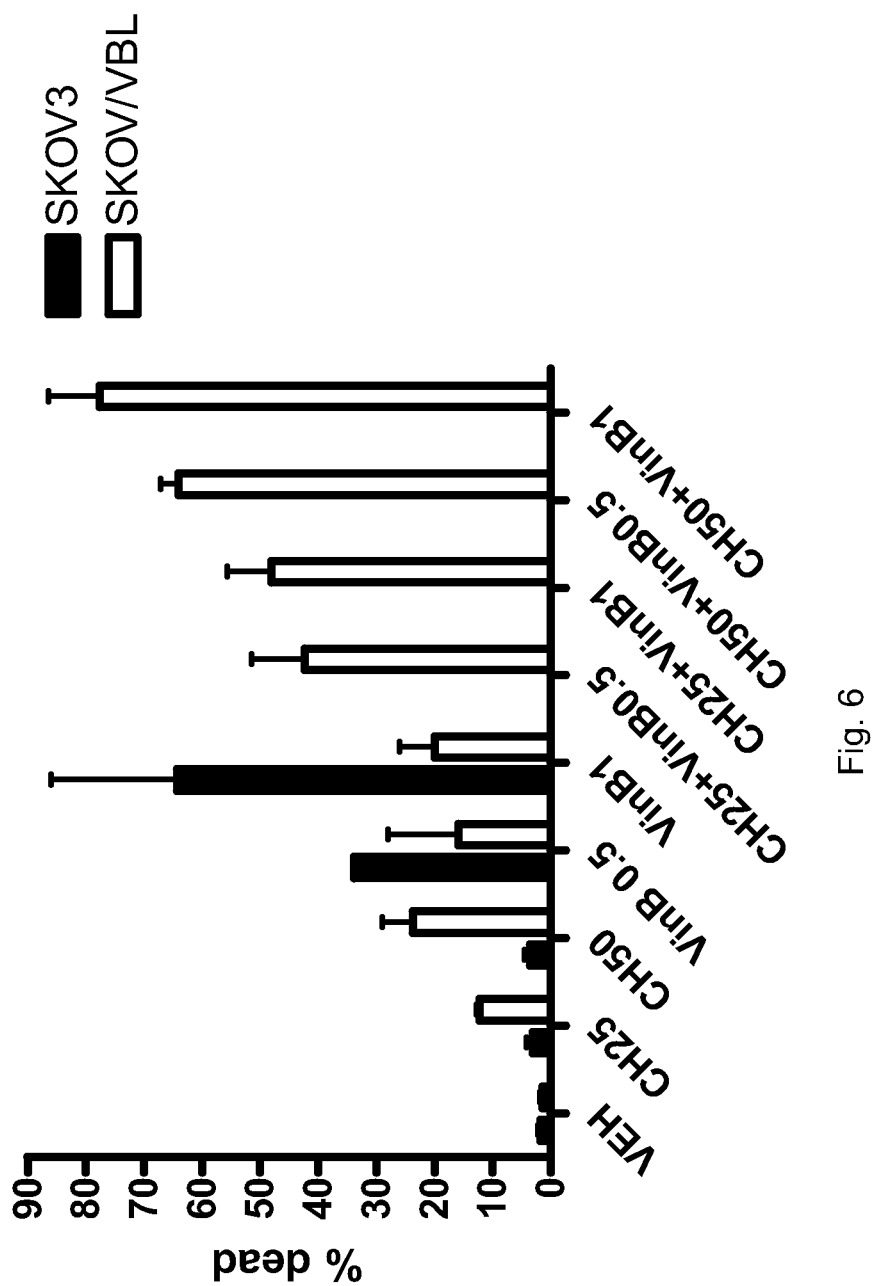
FIG. 6 illustrates a graph showing the potentiation of vinblastine by 5-CHInd in SKOV3 and SKOV/VBL cells.

The potentiation of vinblstine by 5-CHInd was also assessed in MDR negative cesll (SKOV3) and MDR positive SKOV/VBL cells by administering various concentrations of vinblastine and 5-CHInd to the cells. FIG. 6 is a graph illustrating the cytoxic effect of 25 µg/ml of 5-CHInd (CH25), 50 µg/ml of 5-CHInd (CH50), 0.5 µg/ml of vinblastine (VinB 0.5), 1 µg/ml of vinblastine (VinB 1), 25 µg/ml of 5-CHInd in combination with 0.5 µg/ml of vinblastine (CH25+VinB 0.5), 25 µg/ml of 5-CHInd in combination with 1 µg/ml of vinblastine (CH25+VinB 1), 50 µg/ml of 5-CHInd in combination with 0.5 µg/ml of vinblastine (CH50+VinB 0.5), and 50 µg/ml of 5-CHInd in combination with 1 µg/ml of vinblastine (CH50+VinB 1) administered respectively to SKOV3 and SKOV/VBL cells. FIG. 6 shows the potentiation of vinblastine by the 5-CHInd in the cells.

Additionally, a series of control experiments verify the specificity of 5-CHInd as an inhibitor of P-gp. First, it is demonstrated that 5-CHInd potentiates the effects of chemotherapeutic agents such as doxorobucin and paclitaxel that are substrates of P-gp. Conversely, 5-CHInd does not potentiate the effects of cisplatin and 5-fluorouracil since they are not substrates of P-gp. Finally, since staurosporine does not inhibit P-gp, it does not act as a potentiating agent. The lack of potentiation in this case provides further evidence for the selectivity of 5-CHInd in modulating the activity of P-gp to reverse the MDR phenotype.

Molecular Mechanism of P-glycoprotein Inhibition.

The mechanism by which 5-CHInd inhibits P-gp is validated by demonstrating the ability of 5-CHInd to enhance intracellular accumulation of chemotherapeutic agents. Intracellular drug accumulation studies use confluent CEM-C7 and CEM-VBL cells incubated with [$^3$H]-vinblastine (Moravek Biochemicals, Brea, Calif.) in the absence or presence of 5-CHInd. After attainment of equilibrium, cells are harvested and washed to remove any unbound [$^3$H]-vinblastine. Washed cells are then solubized and the retained radioactivity is quantified by liquid scintillation techniques. Measured radioactivity is normalized for protein content, and drug accumulation is expressed as a percentage of the vehicle control. 5-CHInd causes a significant accumulation of [$^3$H]-vinblastine by inhibiting the activity of P-gp to prevent drug efflux.

To measure the effect of 5-CHInd on the efflux of [$^3$H]-vinblastine, CEM-VBL cells are incubated with a sub-lethal dose of 5-CHInd or vehicle (DMSO) followed by the addition of a fixed concentration of [$^3$H]-vinblastine. After attainment of equilibrium, cells are washed and aliquots are analyzed for [$^3$H]-vinblastine accumulation at variable times (5 to 120 minutes). The efflux rate constant is obtained from a fit of the data to $y=Ae^{-kt}$ where y is the amount of radioactivity at time t, A is maximal amplitude in accumulation, k is the efflux rate constant, and t is time.

Results

By inhibiting the drug transport activity of P-gp, 5-CHInd causes a significant accumulation of [$^3$H]-vinblastine in CEM-VBL cells. The accumulation of [$^3$H]-vinblastine corresponds to a decrease in rate constant for drug efflux compared to that of vehicle-treated cells. Control experiments using MDR negative cells (CEM-C7) demonstrate that 5-CHInd has no effect on the accumulation or efflux of [$^3$H]-vinblastine since these cells are devoid of P-gp. Additional control experiments using verapamil as an MDR-inhibitory agent verify accumulation of [$^3$H]-vinblastine is mediated through the inhibition of P-gp. The use of verapamil allows the direct comparison of the efficacy and potency of 5-CHInd versus other characterized P-gp inhibitors. Collectively, these analyses validate that 5-CHInd is an inhibitor of P-gp.

Validation of Kinase Inhibition

Preliminary flow cytomerty data indicated that 5-CHInd induces cell cycle arrest by inhibiting one or more CDKs. This data is confirmed by performing intensive in vitro analyses to define the inhibitory effect of 5-CHInd on the phosphoryl transfer activity of kinase candidates purified forms of CDK1, CDK2, and CDK5, which are commercially available (Sigma-Aldrich, Invitrogen, etc). Classical inhibition studies define the mode of inhibition, for example, competitive, non-competitive, or un-competitive inhibition. Classical inhibition studies are also performed to define the potency of each analog as evaluated by $K_i$ values. Phosphoryl transfer assays monitor the conversion of $\alpha$-$^{32}$P-ATP to $\alpha$-$^{32}$P-ADP using thin layer chromatography. Initial rates in product formation are measured by varying the concentration of ATP at several fixed concentrations of 5-CHInd (the nucleoside form) or various phosphorylated forms (mono, di, or triphosphate nucleosides). Double-recipricol plot analyses of the initial rates versus ATP concentration define the mode of inhibition and determine the $K_i$ value for both analogs. Comparing $K_i$ values amongst various phosphorylated forms of the 5-CHInd indicates which is more potent, a feature that provides insight into the in vitro mechanism of kinase inhibition. In addition, the measured $K_i$ value are compared to $LD_{50}$ values obtained in our cell culture studies to provide insight into the identity of which CDK is inhibited. In general, if the $K_i$ value is significantly higher than the $LD_{50}$ value, then it is unlikely that the CDK in question is the actual in vivo target. The converse observation, i.e., $K_i$ is significantly lower than the $LD_{50}$ value, suggests but not unambiguously proves that the CDK in question is inhibited to ultimately cause cell death.

From the above description of the invention, those skilled in the art will perceive improvements, changes, and modifications. Such improvements, changes, and modifications are intended to be covered by the appended claims. All references, publications, and patents cited herein, are incorporated by reference in their entirety.

Having described the invention, the following is claimed:

1. A method of inhibiting P-glycoprotein activity in a cell expressing P-glycoprotein comprising:

administering a pharmaceutical composition comprising a nucleoside analog having the formula (I):

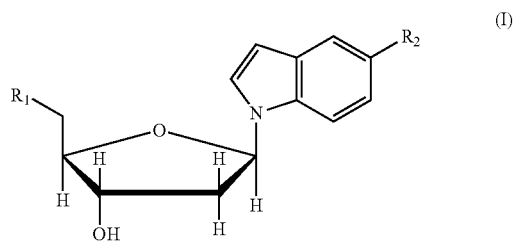

where $R_1$ is OH, monophosphate ($H_2O_3PO$— or ($O_3PO$—)$^{2-}$), diphosphate ($H_3(O_3PO)_2$— or (($O_3PO)_2$—)$^{3-}$), triphosphate ($H_4(O_3PO)_3$—, (($O_3PO)_3$—)$^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative; and where $R_2$ is an unsubstituted or substituted cyclohexyl; a pharmaceutically acceptable salt thereof; or a prodrug thereof.

2. The method of claim 1, the cell comprising a neoplastic cells of a subject.

3. The method of claim 1, the nucleoside analog competitively inhibiting a first chemotherapeutic target by selectively binding the nucleoside analog to an active site of the first chemotherapeutic target; and competitively inhibiting a second chemotherapeutic target by selectively binding the nucleoside analog to an active site of the second chemotherapeutic target.

4. The method of claim 3, wherein the active site of the first chemotherapeutic target and the second chemotherapeutic target are ATP binding regions.

5. The method of claim 3 wherein the first chemotherapeutic target is P-Glycoprotein drug transporter and the second chemotherapeutic target is a cyclin-dependent kinase.

6. The method of claim 5 wherein the cyclin-dependent kinase targeted is selected from a group consisting of CDK1, CDK4, and CDK5 or a combination thereof.

7. The method of claim 2 wherein the nucleoside analog is administered to the subject at a dosage in the range of about 0.001 µg/mL/day to about 100 µg/mL/day.

8. The method of claim 1, the nucleoside analog comprising:

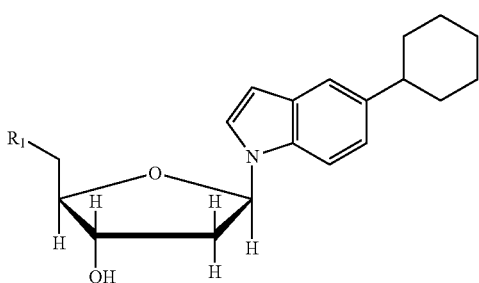

where $R_1$ is OH, monophosphate ($H_2O_3PO$— or ($O_3PO$—)$^{2-}$), diphosphate ($H_3(O_3PO)_2$— or (($O_3PO)_2$—)$^{3-}$), triphosphate ($H_4(O_3PO)_3$—, (($O_3PO)_3$—)$^{4-}$), or $OR_a$, where $R_a$ comprises at least one of a straight chain, branched or cylclic alkyl, CO-alkyl, CO-aryl, CO-alkoxyalkyl, arylsulfonyl, aralkylsulfonyl, amino acid residude, fatty acid residue, or a mono, di, or triphosphate derivative; a pharmaceutically acceptable salt thereof; or a prodrug thereof.

9. A method of treating a neoplastic disorder in a subject comprising:
administering to neoplastic cells of the subject a pharmaceutical composition comprising a nucleoside analog having the formula (I):

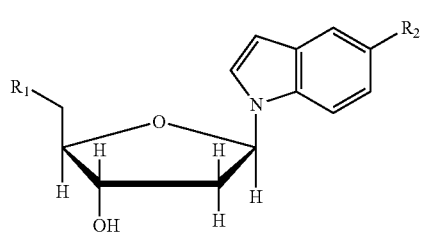

where $R_1$ is OH, monophosphate ($H_2O_3PO$— or ($O_3PO$—)$^{2-}$), diphosphate ($H_3(O_3PO)_2$— or (($O_3PO)_2$—)$^{3-}$), triphosphate ($H_4(O_3PO)_3$—, (($O_3PO)_3$—)$^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residude, fatty acid residue, or a mono, di, or triphosphate derivative; and
where $R_2$ is an unsubstituted or substituted cyclohexyl; a pharmaceutically acceptable salt thereof; or a prodrug thereof.

10. The method of claim 9, the neoplastic cell expressing P-glycoprotein.

11. The method of claim 9, the nucleoside analog competitively inhibiting a first chemotherapeutic target by selectively binding the nucleoside analog to an active site of the first chemotherapeutic target; and competitively inhibiting a second chemotherapeutic target by selectively binding the nucleoside analog to an active site of the second chemotherapeutic target.

12. The method of claim 11, wherein the active site of the first chemotherapeutic target and the second chemotherapeutic target are ATP binding regions.

13. The method of claim 11, wherein the first chemotherapeutic target is P-glycoprotein drug transporter and the second chemotherapeutic target is a cyclin-dependent kinase.

14. The method of claim 13 wherein the cyclin-dependent kinase targeted is selected from a group consisting of CDK1, CDK4, and CDK5 or a combination thereof.

15. The method of claim 9, the nucleoside analog comprising:

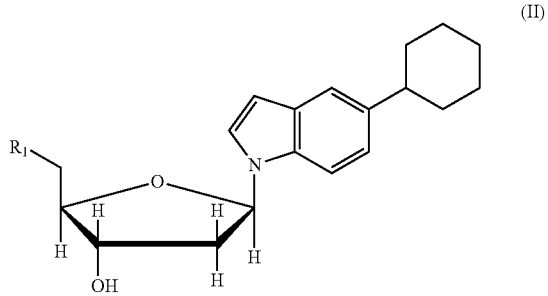

where $R_1$ is OH, monophosphate ($H_2O_3PO$— or ($O_3PO$—)$^{2-}$), diphosphate ($H_3(O_3PO)_2$— or (($O_3PO)_2$—)$^{3-}$), triphosphate ($H_4(O_3PO)_3$—, (($O_3PO)_3$—)$^{4-}$), or $OR_a$, where $R_a$ comprises at least one of a straight chain, branched or cylclic alkyl, CO-alkyl, CO-aryl, CO-alkoxyalkyl, arylsulfonyl, aralkylsulfonyl, amino acid residude, fatty acid residue, or a mono, di, or triphosphate derivative; a pharmaceutically acceptable salt thereof; or a prodrug thereof.

16. The method of claim 10, further administring another therapeutic agent in conjunction with the nucleoside analog.

17. The method of claim 16, the other therapeutic agents comprising at least one of a chemotherapeutic agent, an antimetabolite, an antitumorgenic agent, an antimitotic agent, an antiviral agent, an antineoplastic agent, an immunotherapeutic agent, and a radiotherapeutic agent.

18. The method of claim 10, the other therapeutic agent being a substrate for P-glycoprotein.

19. A method of potentiating the cytotoxic effect of chemotherapeutic agents on multiple drug resistant neoplastic cells, the method comprising: administering a nucleoside analog to the subject in conjunction with administering a chemotherapeutic agent; the nucleoside analog having the formula (I):

(I)

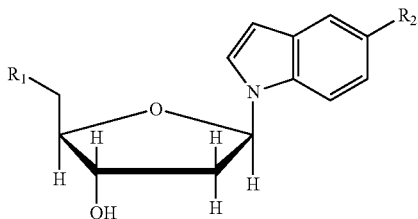

where $R_1$ is OH, monophosphate ($H_2O_3PO-$ or ($O_3PO-$)$^{2-}$), diphosphate ($H_3(O_3PO)_2-$ or (($O_3PO)_2-$)$^{3-}$), triphosphate ($H_4(O_3PO)_3-$, (($O_3PO)_3-$)$^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative; and where $R_2$ is an unsubstituted or substituted cyclohexyl; a pharmaceutically acceptable salt thereof; or a prodrug thereof.

20. The method of claim 19, the chemotherapeutic agent at least one of an antimetabolite, an antitumorgenic agent, an antimitotic agent, an antiviral agent, an antineoplastic agent, an immunotherapeutic agent, or a radiotherapeutic agent.

21. The method of claim 19, the chemotherapeutic agent being a substrate for P-glycoprotein.

22. The method of claim 19, the nucleoside analog comprising:

(II)

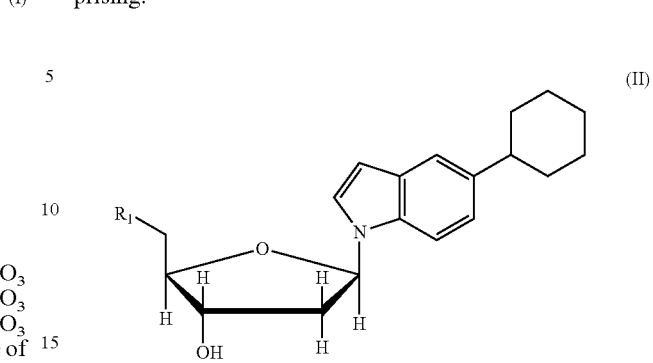

where $R_1$ is OH, monophosphate ($H_2O_3PO-$ or ($O_3PO-$)$^{2-}$), diphosphate ($H_3(O_3PO)_2-$ or (($O_3PO)_2-$)$^{3-}$), triphosphate ($H_4(O_3PO)_3-$, (($O_3PO)_3-$)$^{4-}$), or $OR_a$, where $R_a$ comprises at least one of a straight chain, branched or cylclic alkyl, CO-alkyl, CO-aryl, CO-alkoxyalkyl, arylsulfonyl, aralkylsulfonyl, amino acid residude, fatty acid residue, or a mono, di, or triphosphate derivative; a pharmaceutically acceptable salt thereof; or a prodrug thereof.

* * * * *